United States Patent [19]

Vogt et al.

[11] Patent Number: 5,753,024

[45] Date of Patent: May 19, 1998

[54] GREY PIGMENTS CONTAINING TIN

[75] Inventors: Reiner Vogt, Darmstadt; Klaus Bernhard, Gross-Umstadt; Gerhard Pfaff, Müster; Matthias Kuntz, Ober-Ramstadt; Susanne Rudolph, Dieburg; Sylvia Schmidt, Pfungstadt, all of Germany

[73] Assignee: Merck Patent Gesellschaft mit beschrankter Haftung, Germany

[21] Appl. No.: 666,084

[22] Filed: Jun. 19, 1996

[30] Foreign Application Priority Data

Jun. 20, 1995 [DE] Germany ............... 195 22 267.9

[51] Int. Cl.⁶ ............... C09C 1/00; C09C 1/44
[52] U.S. Cl. ............ 106/417; 106/400; 106/415; 106/436; 106/441; 106/447; 106/461; 106/472; 106/499; 106/501.1; 428/363; 428/403
[58] Field of Search ................ 106/400, 401, 106/415, 417, 436, 441, 442, 447, 461, 903, 501.1, 472, 499; 424/401; 428/363, 403

[56] References Cited

U.S. PATENT DOCUMENTS

| 4,076,551 | 2/1978 | Bernhard et al. | 427/218 |
| 5,271,771 | 12/1993 | Franz et al. | 106/474 |
| 5,501,731 | 3/1996 | Schmid et al. | 106/415 |
| 5,536,447 | 7/1996 | Pfaff et al. | 106/400 |

OTHER PUBLICATIONS

Abstract of DE 41 04 846, Feb. 16, 1991.

Abstract of EP 499,864, Sep. 6, 1995.

Abstract of DE 43 23 747, Jul. 15, 1993.

*Primary Examiner*—Michael Marcheschi
*Attorney, Agent, or Firm*—Millen, White, Zelano & Branigan, P.C.

[57] ABSTRACT

Tin-containing grey pigments of high opacity, processes for their preparation and use thereof.

12 Claims, No Drawings

GREY PIGMENTS CONTAINING TIN

The present invention relates to tin-containing grey pigments of high opacity, to processes for their preparation and to the use thereof.

BACKGROUND OF THE INVENTION

It is known that by incorporating carbon into pigments it is possible to obtain special color effects. Carbon-containing pigments are therefore used both in pigmenting varnishes, powder coatings, paints, printing inks, plastics and the like and in cosmetic preparations. Some of the processes known from the prior art for the preparation of these pigments, however, are hampered by considerable disadvantages.

At present the only way to prepare combinations of carbon-metal oxide mica pigments is to apply carbon from aqueous suspension using suitable surface-active auxiliaries or by pyrolysis of organic compounds. DE-B 11 65 182 describes a complex pyrolysis process in which the carbon is deposited, naturally, only on the pigment surface. In DE-C 25 57 796, the disadvantage of the complex pyrolysis process is no longer present. In the process described therein, a substance is first of all mixed with a dispersion of carbon black. By adding a metal salt solution under hydrolysis conditions, a layer of metal hydroxide containing carbon black is precipitated onto the substrate. The pigments produced in this way are separated off and dried at 130°–150° C. The pigments thus produced, however, are unsuitable for various applications since they are of inadequate abrasion resistance. This characteristic is extremely undesirable especially for incorporation into cosmetic preparations. By calcining the pigments at temperatures of 700°–900° C. in the absence of oxygen it is possible to improve the abrasion resistance (DE-A 41 04 846). In DE-A 41 25 134, carbon-containing compounds are pyrolyzed in the presence of metal oxide platelets or platelet-shaped substrates coated with metal oxides, under conditions in which the metal of the metal oxide is reduced.

DE-A 43 23 747 discloses carbon-containing luster pigments in which the layer of carbon is formed by the thermal decomposition of dextrose at from 100° to 700° C.

In the processes known from the prior art, the carbon is not deposited quantitatively; that is to say it is partially present in the form of agglomerates on the pigment, with the result that the pigments do not exhibit good opacity. The improperly deposited carbon must be removed by sedimentation, a time-consuming and costly procedure.

A further disadvantage is the frequently observed bleeding of the carbon when the pigments are suspended in organic solvents for the preparation of coating systems.

Furthermore, these pigments have a brownish character and are notable for a severe loss in luster, caused by absorption and scattering phenomena by the coarse-particled, precipitated carbon agglomerates.

There was therefore a need for the preparation of carbon-containing grey pigments of enhanced abrasion resistance and stability to bleeding and high gloss, without the requirement of great technical complexity. It has been possible to achieve this object by means of the present invention.

SUMMARY OF THE INVENTION

It has surprisingly now been found that pigments comprising metallic tin in addition to carbon have enhanced abrasion resistance, high opacity and special color effects. The grey pigments of the invention are obtained when substrates coated with tin dioxide and at least one further metal oxide and with organic colloids are calcined at temperatures of 900°–1100° C.

Such high pyrolysis temperatures are accompanied on the one hand by the decomposition of the organic colloid particles, with the formation of very fine particles of carbon in the metal oxide layer, and on the other hand the reduction of the tin dioxide.

The invention thus provides tin-containing grey pigments which are obtainable by pyrolysis of substrates which are coated with tin dioxide and at least one further metal oxide and colloidal organic particles at temperatures of 900°–1100° C. in the absence of oxygen.

The invention also provides a process for the preparation of the tin-containing grey pigments, characterized in that an aqueous substrate suspension is prepared, a hydrolyzable tin salt solution is added, one or more further hydrolyzable metal salt solutions are added and an aqueous organic colloid solution is added, the pH of the substrate suspension being maintained by simultaneous addition of a base or an acid within a range which brings about hydrolysis of the metal salt, and the finished substrate is separated off, washed, dried and calcined at temperatures of 900°–1100° C. in the absence of oxygen. The hydrolyzable metal salt solution(s) and aqueous organic colloid solution are preferably added simultaneously but separately and the tin salt solution is either added before the other two or simultaneously therewith.

Upon further study of the specification and appended claims, further objects and advantages of this invention will become apparent to those skilled in the art.

Suitable base substrates for the coating are on the one hand opaque and on the other hand transparent non-platelet-shaped substrates. Preferred substrates are phyllosilicates and platelet-shaped materials optionally coated with metal oxides. Particularly suitable substrates are mica, talc, kaolin, bismuth oxychloride, flakes made of glass, $BaSO_4$, $SiO_2$ or of synthetic ceramics, or other comparable materials. Also suitable are metal flakes, for example aluminum flakes, or platelet-shaped metal oxides, for example platelet-shaped iron oxide and micas coated with colored or colorless metal oxides, alone or as a mixture in one single layer or in successive layers. These pigments, known as pearl luster pigments, are disclosed for example in German patents and patent applications 14 67 468, 19 59 998, 20 09 566, 22 14 545, 22 15 191, 22 44 298, 23 13 331, 25 22 572, 31 37 808, 31 37 809, 31 51 343, 31 51 354, 31 51 355, 32 11 602 and 32 35 017.

The platelet-shaped substrates preferably have a thickness of from about 0.1 to 5 μm and, in particular, from 0.2 to 4.5 μm. The extent in the two other dimensions is preferably from about 1 to 250 μm, in particular from 2 to 200 μm.

In preparing the carbon-containing pigments according to the invention, an aqueous suspension of the substrate is prepared first of all. A solution of at least one metal salt can be introduced, if desired, into this suspension. An aqueous tin salt solution is added. Either during or after addition of the aqueous tin salt solution, the simultaneous but separate addition of a further metal salt solution and of the organic colloid solution is performed, the pH of the reaction mixture being maintained, by simultaneous addition of an acid or base, within a range which brings about hydrolysis of the metal salt. In this procedure, a metal oxide and/or hydroxide mixture is precipitated onto the substrate surface together with the colloid particles doped therein.

By varying the thickness of the doped metal oxide layer it is possible, especially in the case of platelet-shaped substrates coated with titanium dioxide, to obtain any desired first-order or higher-order interference colors. The thickness of the carbon-doped metal oxide layer is not itself critical, and is in general from about 1 to 400 nm, preferably from 5 to 200 nm.

The metal salts can be precipitated using any acid or base. The optimum concentrations and pH values can be determined by routine experiments. Usually, once a pH has been established for the precipitation, it is retained throughout the precipitation in order to obtain uniform pigments.

It is expedient to use those bases which are easy to obtain industrially, for example NaOH, KOH or ammonia, and as acids to use dilute mineral acids, for example HCl, $H_2SO_4$ or $HNO_3$. Since the bases and acids serve only to alter the pH, their character is not critical, and so other acids and bases may be employed.

After the separation, washing and drying of the substrates coated in this way, the pigments are calcined at temperatures of 900°–1100° C. in the absence of oxygen, during which calcination decomposition of the organic colloid particles and reduction take place. The calcination temperature depends in general on the precipitated layer thickness; the period of calcining may be from several minutes to several hours, but is preferably from 20 to 120 minutes.

As metal salts from which the metal oxides and/or metal hydroxides can be precipitated it is possible to use all water-soluble salts which can be hydrolyzed by bases or acids. In general, alkaline hydrolysis is preferred. Particularly suitable metal salts are those of aluminum, titanium, zirconium, iron, chromium, nickel, cobalt and/or tin, preferably titanium. For the tin salts, preference is given to employing the chlorides, and also the sulfates and nitrates.

The specific process parameters for the coating and for hydrolysis of the metal salt are of the customary type and are described, for example, in DE 25 57 796. All other parameters, for example particle size, concentrations of metal salt, temperatures and preferred embodiments, can likewise be taken from DE 25 27 796.

If desired, the pigments of the invention can also be aftercoated, preferably before the calcination.

Essential constituents of the coating composition are the tin oxide, preferably tin dioxide, and the organic colloid particles. All known organic colloids having particle dimensions<$10^{-5}$ cm can be used. Preferably, the organic colloids have particle dimensions of 1–1000 nm. Preference is given to the use of readily water-soluble, colloidal organic particles, for example polysaccharides, starch, cellulose, dextrin or gelatin, and derivatives thereof. The proportion of colloid particles in the metal oxide layer is from 0.01 to 20% by weight, preferably from 0.1 to 10% by weight, based on the overall pigment.

During the pyrolysis under inert conditions, i.e., in the absence of oxygen, the colloid in the metal oxide layer breaks down to give an extremely finely divided carbon with dimensions<5 nm. The carbon is uniformly distributed in the metal oxide layer. Interstices between the metal oxides are filled out to produce an extremely compact carbon/metal oxide layer of high opacity.

The carbon content of the metal oxide layer can be controlled by the quantity of colloidal particles which are applied to the substrate surface together with the metal oxide.

The proportion of carbon in the pigments according to the invention is in general from about 0.01 to 10% by weight, preferably from 0.1 to 5% by weight and, in particular, from 0.1 to 1% by weight, based on the overall pigment.

Because of the different substrates, the proportion of carbon by weight in the carbon/metal oxide layer is subject to considerable variation. As the carbon content increases, the pigment takes on an increasingly graphite-like luster.

Bleeding of the carbon caused by organic solvents is not observed since the carbon, owing to the smallness of its particles, is accommodated firmly within the metal oxide layer. The pigments of the invention are also notable for increased luster and their high opacity. In addition, the pigments are stable to weathering and are nonconductive.

Under the drastic conditions of pyrolysis, all or part—depending on the pyrolysis temperature—of the tin dioxide present in the metal oxide mixture is reduced to metallic tin. The tin content of the pigments depends, in this context, both on the concentration of the tin salt solution employed and on the pyrolysis temperature. The pigments of the invention preferably contain from 0.1 to 10% by weight, in particular from 0.1 to 1% by weight, of metallic tin.

Particular preference is given to pigments whose base substrate is covered with a carbon-containing $TiO_2$ layer which contains from 0.1 to 1% by weight of metallic tin. Grey pigments of this kind exhibit an interesting blue tinge. Under the preferred reaction conditions specified, the $TiO_2$ is present predominantly in rutile form.

The pigments prepared in accordance with the invention are abrasion-resistant, readily dispersible and of very good opacity, so that they can be employed for a variety of purposes, in particular for automotive finishes, for printing inks and in cosmetics.

As a consequence, the invention also provides for the use of the carbon-containing pigments in formulations such as paints, varnishes, powder coatings, printing inks, plastics and cosmetics.

The invention provides, furthermore, formulations comprising the pigments according to the invention.

Without further elaboration, it is believed that one skilled in the art can, using the preceding description, utilize the present invention to its fullest extent. The following preferred specific embodiments are, therefore, to be construed as merely illustrative, and not limitative of the remainder of the disclosure in any way whatsoever.

In the foregoing and in the following examples, all temperatures are set forth uncorrected in degrees Celsius and unless otherwise indicated, all parts and percentages are by weight.

The entire disclosure of all applications, patents and publications, cited above and below, and of corresponding German application 195 22 267.9, filed Jun. 20, 1995, are hereby incorporated by reference.

EXAMPLES

The examples which follow are intended to illustrate the invention in more detail without, however, limiting it:

Example 1

100 g of mica with a particle size of 10–60 µm are suspended in 2 l of water and the suspension is heated to 75° C. A solution consisting of 4.5 g of $SnCl_4 \times 5H_2O$ and 15 ml of 37% HCl in 60 ml of water is metered into the mica suspension. During the addition, the pH is held constant with 32% NaOH solution. After the end of the addition of the $SnCl_4$ solution, 210 ml of $TiCl_4$ solution (400 g of $TiCl_4$/l of water) and the gelatin solution (4 g dissolved in 400 ml of water) are metered simultaneously but separately into the pigment suspension. During the covering procedure the pH is held constant by adding 32% NaOH solution.

After the end of the addition, the mixture is stirred at 75° C. for 15 minutes. The pH is adjusted to 6.0 using 32% NaOH solution and the pigment suspension is stirred for a further 15 minutes without heating. The finished pigment is filtered off, washed free from salt, dried at 150° C. and finally calcined at 950° C. for 60 minutes in a nitrogen atmosphere.

A pigment with a silver interference color is obtained. The mass tone is grey and, when tilted at shallow angles, shows a blue tinge.

Example 2

100 g of mica with a particle size of 10–60 μm are suspended in 2 l of water and the suspension is heated to 75° C. A solution consisting of 4.5 g of $SnCl_4 \times 5H_2O$ and 15 ml of 37% HCl in 60 ml of water is metered into the mica suspension. During the addition, the pH is held constant with 32% NaOH solution. After the end of the addition of the $SnCl_4$ solution, 210 ml of $TiCl_4$ solution (400 g of $TiCl_4$/l of water) and the dextrin solution (4 g dissolved in 400 ml of water) are metered simultaneously but separately into the pigment suspension. During the covering procedure the pH is held constant by adding 32% NaOH solution.

After the end of the addition, the mixture is stirred at 75° C. for 15 minutes. The pH is adjusted to 6.0 using 32% NaOH solution and the pigment suspension is stirred for a further 15 minutes without heating. The finished pigment is filtered off, washed free from salt, dried at 150° C. and finally calcined at 950° C. for 60 minutes in a nitrogen atmosphere.

A pigment with a silver interference color is obtained. The mass tone is grey and, when tilted at shallow angles, shows a blue tinge.

The preceding examples can be repeated with similar success by substituting the generically or specifically described reactants and/or operating conditions of this invention for those used in the preceding examples.

From the foregoing description, one skilled in the art can easily ascertain the essential characteristics of this invention, and without departing from the spirit and scope thereof, can make various changes and modifications of the invention to adapt it to various usages and conditions.

What is claimed is:

1. A tin-containing grey pigment prepared by pyrolysis of a substrate with a coating comprising tin dioxide, at least one further metal oxide and/or hydroxide and colloidal organic particles at a temperature of 900°–1100° C. in the absence of oxygen.

2. A tin-containing grey pigment according to claim 1, wherein the pigment contains metallic tin from pyrolysis of tin dioxide in an amount from 0.01 to 10% by weight, based on the total pigment.

3. A tin-containing grey pigment according to claim 1, wherein the substrate is platelet-shaped.

4. A tin-containing grey pigment according to claim 2, wherein the substrate is platelet-shaped.

5. A tin-containing grey pigment according to claim 3, wherein the platelet-shaped substrate is mica platelets, glass flakes, $BaSO_4$ flakes, $SiO_2$ flakes synthetic ceramic flakes, or mica platelets coated with one or more metal oxides.

6. A tin-containing grey pigment according to claim 4, wherein the platelet-shaped substrate is mica platelets, glass flakes, $BaSO_4$ flakes, $SiO_2$ flakes, synthetic ceramic flakes, or mica platelets coated with one or more metal oxides.

7. A tin-containing grey pigment according to claim 1, wherein the colloidal organic particles are starch, cellulose, gelatin, dextrin or a derivative of starch, cellulose, gelatin or dextrin.

8. A process for the preparation of a tin-containing grey pigment, comprising adding to an aqueous substrate solution a hydrolyzable tin salt solution, further adding one or more other hydrolyzable metal salt solutions and an aqueous organic colloid solution to produce a suspension, maintaining a pH of the suspension by simultaneous addition of a base or an acid within a range which brings about hydrolysis of the metal salts, separating, washing and drying a resulting coated substrate and calcining the resulting coated substrate at a temperature of 900°–1100°C. in the absence of oxygen.

9. A process according to claim 8, wherein the other hydrolyzable metal salt is a titanium salt.

10. A paint, varnish, powder coating, printing ink or cosmetic composition comprising a grey pigment according to claim 1.

11. A pigment produced by a process of claim 8.

12. A pigment according to claim 1, comprising a layer of carbon doped with tin.

* * * * *